US012697088B2

(12) United States Patent
　　　Galeotti et al.

(10) Patent No.:　　US 12,697,088 B2
(45) Date of Patent:　　　　Aug. 4, 2026

---

(54) SYSTEM AND METHOD FOR TRACKING A CURVED NEEDLE

(71) Applicant: Carnegie Mellon University, Pittsburgh, PA (US)

(72) Inventors: John Michael Galeotti, Pittsburgh, PA (US); Wanwen Chen, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 403 days.

(21) Appl. No.: 18/283,928

(22) PCT Filed: Mar. 24, 2022

(86) PCT No.: PCT/US2022/021648
§ 371 (c)(1),
(2) Date: Sep. 25, 2023

(87) PCT Pub. No.: WO2022/204348
PCT Pub. Date: Sep. 29, 2022

(65) Prior Publication Data
US 2024/0164742 A1　　May 23, 2024

Related U.S. Application Data

(60) Provisional application No. 63/165,297, filed on Mar. 24, 2021.

(51) Int. Cl.
*A61B 8/08*　　　　(2006.01)
*A61B 8/00*　　　　(2006.01)
(Continued)

(52) U.S. Cl.
CPC .......... *A61B 8/0841* (2013.01); *A61B 8/5223* (2013.01); *A61B 17/3403* (2013.01);
(Continued)

(58) Field of Classification Search
None
See application file for complete search history.

(56) References Cited

U.S. PATENT DOCUMENTS 10,136,915 B2 *　11/2018　Liu ...................... A61B 8/0891
2010/0056900 A1 *　3/2010　Whitcomb ............. A61B 90/11
　　　　　　　　　　　　　　　　　　　　　600/414
(Continued)

OTHER PUBLICATIONS

Li et al., "Tip Estimation Method in Phantoms for Curved Needle Using 2D Transverse Ultrasound Images", Applied Sciences, 2019, pp. 1-17.

*Primary Examiner* — Darryl V Dottin
(74) *Attorney, Agent, or Firm* — The Webb Law Firm

(57)　　　　ABSTRACT

Provided is a system, method, and computer program product for tracking a needle. The method includes determining a visibility of the needle being inserted into a subject in an image of a sequence of images, in response to determining that the visibility satisfies a visibility threshold, detecting a location of the needle based on at least one first algorithm and a detected curvature of the needle, in response to determining that the visibility does not satisfy the visibility threshold, detecting the location of the needle being inserted based on at least one second algorithm, and tracking the location of the needle in the sequence of images based on locations detected with the at least one first algorithm and the at least one second algorithm.

20 Claims, 5 Drawing Sheets

(51) Int. Cl.
    *A61B 17/34*         (2006.01)
    *A61B 34/20*         (2016.01)
    *G06T 7/246*         (2017.01)
(52) U.S. Cl.
    CPC .............. *A61B 34/20* (2016.02); *G06T 7/246*
        (2017.01); *A61B 2017/3413* (2013.01); *A61B*
          *2034/2063* (2016.02); *G06T 2207/10016*
                                (2013.01)

(56) References Cited

U.S. PATENT DOCUMENTS

| | | | |
|---|---|---|---|
| 2014/0031674 A1* | 1/2014 | Newman .............. | A61B 8/0841 |
| | | | 600/424 |
| 2014/0039316 A1* | 2/2014 | Ichioka ................... | A61B 8/13 |
| | | | 600/443 |
| 2014/0187942 A1 | 7/2014 | Wang et al. | |
| 2020/0178927 A1* | 6/2020 | Patton ................. | A61B 8/0841 |
| 2020/0205774 A1* | 7/2020 | Duffy ................... | A61B 8/5223 |

* cited by examiner

SYSTEM AND METHOD FOR TRACKING A CURVED NEEDLE

CROSS REFERENCE TO RELATED APPLICATIONS

This application is the United States national phase of International Application No. PCT/US22/21648, filed Mar. 24, 2022, and claims priority to U.S. Provisional Patent Application No. 63/165,297, filed Mar. 24, 2021, the disclosures of which are hereby incorporated by reference in their entireties.

GOVERNMENT LICENSE RIGHTS

This invention was made with Government support under W81XWH-19-C-0083 awarded by U.S. Army Medical Research Activity. The Government has certain rights in the invention.

BACKGROUND

1. Field

This disclosure relates generally to tracking the motion a curved needle and, in non-limiting embodiments, to systems and methods for tracking curved needles in a sequence of images. The curved needle may be a straight needle that has undergone needle bending during insertion due to forces from tissues and/or the like.

2. Technical Considerations

Percutaneous intervention is a common practice in medical treatment, such as blood sampling, biopsies, and anesthesia. Robotic needle insertion is a promising application of medical robots, and research in improving the robot insertion planning and control methods have been reported in previous years. Medical images can be used in robot feedback to achieve more accurate and robust control. Ultrasound imaging is the most common technique in this procedure because ultrasound can provide safe real-time imaging with a smaller workspace and lower cost. Previous research in ultrasound-based needle tracking assumes that the needle is a straight line with strong intensity in the images. Line detection methods are used, such as Hough Transform and random sample consensus (RANSAC). However this assumption is not always true. For one, the visibility of needles is influenced by many factors. A lot of factors can influence the appearance of artifacts in ultrasound images, such as the size and placement of the needle and the properties of the transducer. Part or all of the needle might not be directly visible during some or all of the insertion. Detecting the micro-motion of tissue can help localize the non-visible needle or part thereof. Other techniques use a Histogram-of-Gradients approach to detect tissue motion and estimate needle location. Support Vector Machines have also been used to locate a non-visible needle based on time-domain features.

During needle tracking, needles can bend due to the interaction with soft tissue. The needle deflection due to the forces from interaction can cause inaccuracy in percutaneous therapies. Previous research models the curved needle and estimates the curvature in different ways. In two-dimensional (2D) ultrasound, there are two scanning modes: transverse (out-of-plane) scanning and longitudinal (in-plane) scanning. In transverse scanning, ultrasound needle localization and robot scanning kinematics are combined to estimate needle three-dimensional (3D) curvature from a 2D ultrasound image. Needle cross section localization and RANSAC fitting is used in some techniques to fit a curved needle. Scanning curved needles in the longitudinal plane is difficult because the misalignment of the needle axis and the image plane can degrade the image quality.

SUMMARY

According to non-limiting embodiments or aspects, provided is a method for tracking a needle, comprising: determining a visibility of the needle being inserted into a subject in an image of a sequence of images; in response to determining that the visibility satisfies a visibility threshold, detecting a location of the needle based on at least one first algorithm and a detected curvature of the needle; in response to determining that the visibility does not satisfy the visibility threshold, detecting the location of the needle being inserted based on at least one second algorithm; and tracking the location of the needle in the sequence of images based on locations detected with the at least one first algorithm and the at least one second algorithm.

In non-limiting embodiments or aspects, wherein detecting the location of the needle based on the at least one first algorithm comprises: determining a length of a visible portion of the needle being inserted into the subject; in response to determining that the length satisfies a length threshold, detecting the location of the needle based on a weighted polynomial fitting algorithm and the detected curvature of the needle; and in response to determining that the length does not satisfy the length threshold, detecting the location of the needle based on a straight needle tracking algorithm. In non-limiting embodiments or aspects, wherein detecting the location of the needle based on the weighted polynomial fitting algorithm comprises: segmenting the image by identifying candidate pixels corresponding to the needle based on an intensity threshold; weighing each pixel of the candidate pixels based on a normalized intensity, a gradient magnitude, and a distance to an estimated location of a tip of the needle; and fitting a curve to the candidate pixels based on weights of at least a portion of pixels of the candidate pixels. In non-limiting embodiments or aspects, the method further comprises: filtering the image after identifying the candidate pixels and before weighing each pixel; and identifying additional candidate pixels based on connections to the candidate pixels.

In non-limiting embodiments or aspects, wherein detecting the location of the needle based on the straight needle tracking algorithm comprises: adjusting a location of a tip of the needle and/or an insertion point of the needle. In non-limiting embodiments or aspects, adjusting the location of the tip and/or the insertion point comprises: extending a line corresponding to a visual portion of the needle in a first direction to a side of the image; extending the line in a second direction opposite the first direction until a length of the line matches a length of the needle in a previous image in the sequence of images; and identifying the tip of the needle in a range of pixels surrounding an end of the line. In non-limiting embodiments or aspects, wherein detecting the location of the needle being inserted based on the at least one second algorithm comprises: calculating a histogram gradient for each cell in the image; and detecting a deformation of tissue based on the histogram gradient of each cell for the image and a static background image. In non-limiting embodiments or aspects, wherein detecting the location of the needle being inserted based on the at least one second algorithm comprises: estimating, with a kinematics tracking algorithm, a location of a tip of the needle based on kinematics data and a compensation factor based on a confidence score. In non-limiting embodiments or aspects, wherein detecting the location of the needle based on the at least one first algorithm and the detected curvature of the needle comprises: estimating a main axis of a region of interest including the needle. In non-limiting embodiments or aspects, the method further comprises: in response to determining that the visibility satisfies a visibility threshold, updating kinematics information associated with the at least one second algorithm.

According to non-limiting embodiments or aspects, provided is a method for tracking a needle, comprising: determining a visibility of the needle being inserted into a subject by a robot in an image of a sequence of images; in response to determining that the visibility satisfies a visibility threshold, calibrate and/or recalibrate kinematics information associated with the robot; in response to determining that the visibility does not satisfy the visibility threshold, detecting the location of the needle being inserted based on at least one second algorithm and the kinematics information; and tracking the location of the needle in the sequence of images based on the location of the needle.

According to non-limiting embodiments or aspects, provided is a system for tracking a needle, comprising at least one computing device programmed or configured to: determine a visibility of the needle being inserted into a subject in an image of a sequence of images; in response to determining that the visibility satisfies a visibility threshold, detect a location of the needle based on at least one first algorithm and a detected curvature of the needle; in response to determining that the visibility does not satisfy the visibility threshold, detect the location of the needle being inserted based on at least one second algorithm; and track the location of the needle in the sequence of images based on locations detected with the at least one first algorithm and/or the at least one second algorithm as continuously or continually determined based on comparing the visibility of the needle to the visibility threshold.

In non-limiting embodiments or aspects, wherein detecting the location of the needle based on the at least one first algorithm comprises: determining a length of a visible portion of the needle being inserted into the subject; in response to determining that the length satisfies a length threshold, detecting the location of the needle based on a weighted polynomial fitting algorithm and the detected curvature of the needle; and in response to determining that the length does not satisfy the length threshold, detecting the location of the needle based on a straight needle tracking algorithm. In non-limiting embodiments or aspects, wherein detecting the location of the needle based on the weighted polynomial fitting algorithm comprises: segmenting the image by identifying candidate pixels corresponding to the needle based on an intensity threshold; weighing each pixel of the candidate pixels based on a normalized intensity, a gradient magnitude, and a distance to an estimated location of a tip of the needle; and fitting a curve to the candidate pixels based on weights of at least a portion of pixels of the candidate pixels. In non-limiting embodiments or aspects, the at least one computing device is further configured to: filter the image after identifying the candidate pixels and before weighing each pixel; and identify additional candidate pixels based on connections to the candidate pixels.

In non-limiting embodiments or aspects, wherein detecting the location of the needle based on the straight needle tracking algorithm comprises: adjusting a location of a tip of the needle and/or an insertion point of the needle. In non-limiting embodiments or aspects, wherein adjusting the location of the tip and/or the insertion point comprises: extending a line corresponding to a visual portion of the needle in a first direction to a side of the image; extending the line in a second direction opposite the first direction until a length of the line matches a length of the needle in a previous image in the sequence of images; and identifying the tip of the needle in a range of pixels surrounding an end of the line. In non-limiting embodiments or aspects, wherein detecting the location of the needle being inserted based on the at least one second algorithm comprises: calculating a histogram gradient for each cell in the image; and detecting a deformation of tissue based on the histogram gradient of each cell for the image and a static background image. In non-limiting embodiments or aspects, wherein detecting the location of the needle being inserted based on the at least one second algorithm comprises: estimating, with a kinematics tracking algorithm, a location of a tip of the needle based on kinematics data and a compensation factor based on a confidence score. In non-limiting embodiments or aspects, wherein detecting the location of the needle based on the at least one first algorithm and the detected curvature of the needle comprises: estimating a main axis of a region of interest including the needle. In non-limiting embodiments or aspects, the at least one computing device is further configured to: in response to determining that the visibility satisfies a visibility threshold, updating kinematics information associated with the at least one second algorithm.

According to non-limiting embodiments or aspects, provided is a computer program product for tracking a needle, comprising at least one non-transitory computer-readable medium including instructions that, when executed by at least one computing device, cause the at least one computing device to: determine a visibility of the needle being inserted into a subject in an image of a sequence of images; in response to determining that the visibility satisfies a visibility threshold, detect a location of the needle based on at least one first algorithm and a detected curvature of the needle; in response to determining that the visibility does not satisfy the visibility threshold, detect the location of the needle being inserted based on at least one second algorithm; and track the location of the needle in the sequence of images based on locations detected with the at least one first algorithm and/or the at least one second algorithm as continuously or continually determined based on comparing the visibility of the needle to the visibility threshold.

In non-limiting embodiments or aspects, wherein detecting the location of the needle based on the at least one first algorithm comprises: determining a length of a visible portion of the needle being inserted into the subject; in response to determining that the length satisfies a length threshold, detecting the location of the needle based on a weighted polynomial fitting algorithm and the detected curvature of the needle; and in response to determining that the length does not satisfy the length threshold, detecting the location of the needle based on a straight needle tracking algorithm. In non-limiting embodiments or aspects, wherein detecting the location of the needle based on the weighted polynomial fitting algorithm comprises: segmenting the image by identifying candidate pixels corresponding to the needle based on an intensity threshold; weighing each pixel of the candidate pixels based on a normalized intensity, a gradient magnitude, and a distance to an estimated location of a tip of the needle; and fitting a curve to the candidate pixels based on weights of at least a portion of pixels of the candidate pixels. In non-limiting embodiments or aspects, the program instructions further cause the at least one computing device to: filter the image after identifying the candidate pixels and before weighing each pixel; and identify additional candidate pixels based on connections to the candidate pixels.

In non-limiting embodiments or aspects, wherein detecting the location of the needle based on the straight needle tracking algorithm comprises: adjusting a location of a tip of the needle and/or an insertion point of the needle. In non-limiting embodiments or aspects, wherein adjusting the location of the tip and/or the insertion point comprises: extending a line corresponding to a visual portion of the needle in a first direction to a side of the image; extending the line in a second direction opposite the first direction until a length of the line matches a length of the needle in a previous image in the sequence of images; and identifying the tip of the needle in a range of pixels surrounding an end of the line. In non-limiting embodiments or aspects, wherein detecting the location of the needle being inserted based on the at least one second algorithm comprises: calculating a histogram gradient for each cell in the image; and detecting a deformation of tissue based on the histogram gradient of each cell for the image and a static background image. In non-limiting embodiments or aspects, wherein detecting the location of the needle being inserted based on the at least one second algorithm comprises: estimating, with a kinematics tracking algorithm, a location of a tip of the needle based on kinematics data and a compensation factor based on a confidence score. In non-limiting embodiments or aspects, wherein detecting the location of the needle based on the at least one first algorithm and the detected curvature of the needle comprises: estimating a main axis of a region of interest including the needle. In non-limiting embodiments or aspects, the program instructions further cause the at least one computing device to: in response to determining that the visibility satisfies a visibility threshold, updating kinematics information associated with the at least one second algorithm.

Further non-limiting embodiments are set forth in the following numbered clauses:

Clause 1: A method for tracking a needle, comprising: determining a visibility of the needle being inserted into a subject in an image of a sequence of images; in response to determining that the visibility satisfies a visibility threshold, detecting a location of the needle based on at least one first algorithm and a detected curvature of the needle; in response to determining that the visibility does not satisfy the visibility threshold, detecting the location of the needle being inserted based on at least one second algorithm; and tracking the location of the needle in the sequence of images based on locations detected with the at least one first algorithm and the at least one second algorithm.

Clause 2: The method of clause 1, wherein detecting the location of the needle based on the at least one first algorithm comprises: determining a length of a visible portion of the needle being inserted into the subject; in response to determining that the length satisfies a length threshold, detecting the location of the needle based on a weighted polynomial fitting algorithm and the detected curvature of the needle; and in response to determining that the length does not satisfy the length threshold, detecting the location of the needle based on a straight needle tracking algorithm.

Clause 3: The method of clauses 1 or 2, wherein detecting the location of the needle based on the weighted polynomial fitting algorithm comprises: segmenting the image by identifying candidate pixels corresponding to the needle based on an intensity threshold; weighing each pixel of the candidate pixels based on a normalized intensity, a gradient magnitude, and a distance to an estimated location of a tip of the needle; and fitting a curve to the candidate pixels based on weights of at least a portion of pixels of the candidate pixels.

Clause 4. The method of clauses 1-3, further comprising: filtering the image after identifying the candidate pixels and before weighing each pixel; and identifying additional candidate pixels based on connections to the candidate pixels.

Clause 5. The method of clauses 1-4, wherein detecting the location of the needle based on the straight needle tracking algorithm comprises: adjusting a location of a tip of the needle and/or an insertion point of the needle.

Clause 6. The method of clauses 1-5, wherein adjusting the location of the tip and/or the insertion point comprises: extending a line corresponding to a visual portion of the needle in a first direction to a side of the image; extending the line in a second direction opposite the first direction until a length of the line matches a length of the needle in a previous image in the sequence of images; and identifying the tip of the needle in a range of pixels surrounding an end of the line.

Clause 7: The method of clauses 1-6, wherein detecting the location of the needle being inserted based on the at least one second algorithm comprises: calculating a histogram gradient for each cell in the image; and detecting a deformation of tissue based on the histogram gradient of each cell for the image and a static background image.

Clause 8. The method of clauses 1-7, wherein detecting the location of the needle being inserted based on the at least one second algorithm comprises: estimating, with a kinematics tracking algorithm, a location of a tip of the needle based on kinematics data and a compensation factor based on a confidence score.

Clause 9. The method of clauses 1-8, wherein detecting the location of the needle based on the at least one first algorithm and the detected curvature of the needle comprises: estimating a main axis of a region of interest including the needle.

Clause 10. The method of clauses 1-9, further comprising: in response to determining that the visibility satisfies a visibility threshold, updating kinematics information associated with the at least one second algorithm.

Clause 11. A method for tracking a needle, comprising: determining a visibility of the needle being inserted into a subject by a robot in an image of a sequence of images; in response to determining that the visibility satisfies a visibility threshold, calibrate and/or recalibrate kinematics information associated with the robot; in response to determining that the visibility does not satisfy the visibility threshold, detecting the location of the needle being inserted based on at least one second algorithm and the kinematics information; and tracking the location of the needle in the sequence of images based on the location of the needle.

Clause 12: A system for tracking a needle, comprising at least one computing device programmed or configured to: determine a visibility of the needle being inserted into a subject in an image of a sequence of images; in response to determining that the visibility satisfies a visibility threshold, detect a location of the needle based on at least one first algorithm and a detected curvature of the needle; in response to determining that the visibility does not satisfy the visibility threshold, detect the location of the needle being inserted based on at least one second algorithm; and track the location of the needle in the sequence of images based on locations detected with the at least one first algorithm and/or the at least one second algorithm as continuously or continually determined based on comparing the visibility of the needle to the visibility threshold.

Clause 13. The system of clause 12, wherein detecting the location of the needle based on the at least one first algorithm comprises: determining a length of a visible portion of the needle being inserted into the subject; in response to determining that the length satisfies a length threshold, detecting the location of the needle based on a weighted polynomial fitting algorithm and the detected curvature of the needle; and in response to determining that the length does not satisfy the length threshold, detecting the location of the needle based on a straight needle tracking algorithm.

Clause 14: The system of clauses 12 or 13, wherein detecting the location of the needle based on the weighted polynomial fitting algorithm comprises: segmenting the image by identifying candidate pixels corresponding to the needle based on an intensity threshold; weighing each pixel of the candidate pixels based on a normalized intensity, a gradient magnitude, and a distance to an estimated location of a tip of the needle; and fitting a curve to the candidate pixels based on weights of at least a portion of pixels of the candidate pixels.

Clause 15. The system of clauses 12-14, the at least one computing device further configured to: filter the image after identifying the candidate pixels and before weighing each pixel; and identify additional candidate pixels based on connections to the candidate pixels.

Clause 16. The system of clauses 12-15, wherein detecting the location of the needle based on the straight needle tracking algorithm comprises: adjusting a location of a tip of the needle and/or an insertion point of the needle.

Clause 17. The system of any of clauses 12-16, wherein adjusting the location of the tip and/or the insertion point comprises: extending a line corresponding to a visual portion of the needle in a first direction to a side of the image; extending the line in a second direction opposite the first direction until a length of the line matches a length of the needle in a previous image in the sequence of images; and identifying the tip of the needle in a range of pixels surrounding an end of the line.

Clause 18: The system of clauses 12-17, wherein detecting the location of the needle being inserted based on the at least one second algorithm comprises: calculating a histogram gradient for each cell in the image; and detecting a deformation of tissue based on the histogram gradient of each cell for the image and a static background image.

Clause 19. The system of clauses 12-18, wherein detecting the location of the needle being inserted based on the at least one second algorithm comprises: estimating, with a kinematics tracking algorithm, a location of a tip of the needle based on kinematics data and a compensation factor based on a confidence score.

Clause 20. The system of clauses 12-19, wherein detecting the location of the needle based on the at least one first algorithm and the detected curvature of the needle comprises: estimating a main axis of a region of interest including the needle.

Clause 21. The system of clauses 12-20, the at least one computing device further configured to: in response to determining that the visibility satisfies a visibility threshold, updating kinematics information associated with the at least one second algorithm.

Clause 22: A computer program product for tracking a needle, comprising: at least one non-transitory computer-readable medium including instructions that, when executed by at least one computing device, cause the at least one computing device to: determine a visibility of the needle being inserted into a subject in an image of a sequence of images; in response to determining that the visibility satisfies a visibility threshold, detect a location of the needle based on at least one first algorithm and a detected curvature of the needle; in response to determining that the visibility does not satisfy the visibility threshold, detect the location of the needle being inserted based on at least one second algorithm; and track the location of the needle in the sequence of images based on locations detected with the at least one first algorithm and/or the at least one second algorithm as continuously or continually determined based on comparing the visibility of the needle to the visibility threshold.

Clause 23. The computer program product of clause 22, wherein detecting the location of the needle based on the at least one first algorithm comprises: determining a length of a visible portion of the needle being inserted into the subject; in response to determining that the length satisfies a length threshold, detecting the location of the needle based on a weighted polynomial fitting algorithm and the detected curvature of the needle; and in response to determining that the length does not satisfy the length threshold, detecting the location of the needle based on a straight needle tracking algorithm.

Clause 24: The computer program product of clauses 22 or 23, wherein detecting the location of the needle based on the weighted polynomial fitting algorithm comprises: segmenting the image by identifying candidate pixels corresponding to the needle based on an intensity threshold; weighing each pixel of the candidate pixels based on a normalized intensity, a gradient magnitude, and a distance to an estimated location of a tip of the needle; and fitting a curve to the candidate pixels based on weights of at least a portion of pixels of the candidate pixels.

Clause 25. The computer program product of clauses 22-24, wherein the program instructions further cause the at least one computing device to: filter the image after identifying the candidate pixels and before weighing each pixel; and identify additional candidate pixels based on connections to the candidate pixels.

Clause 26. The computer program product of clauses 22-25, wherein detecting the location of the needle based on the straight needle tracking algorithm comprises: adjusting a location of a tip of the needle and/or an insertion point of the needle.

Clause 27. The computer program product of clauses 22-26, wherein adjusting the location of the tip and/or the insertion point comprises: extending a line corresponding to a visual portion of the needle in a first direction to a side of the image; extending the line in a second direction opposite the first direction until a length of the line matches a length of the needle in a previous image in the sequence of images; and identifying the tip of the needle in a range of pixels surrounding an end of the line.

Clause 28. The computer program product of clauses 22-27, wherein detecting the location of the needle being inserted based on the at least one second algorithm comprises: calculating a histogram gradient for each cell in the image; and detecting a deformation of tissue based on the histogram gradient of each cell for the image and a static background image.

Clause 29. The computer program product of clauses 22-28, wherein detecting the location of the needle being inserted based on the at least one second algorithm comprises: estimating, with a kinematics tracking algorithm, a location of a tip of the needle based on kinematics data and a compensation factor based on a confidence score.

Clause 30. The computer program product of clauses 22-29, wherein detecting the location of the needle based on the at least one first algorithm and the detected curvature of the needle comprises: estimating a main axis of a region of interest including the needle.

Clause 31. The computer program product of clauses 22-30, wherein the program instructions further cause the at least one computing device to: in response to determining that the visibility satisfies a visibility threshold, updating kinematics information associated with the at least one second algorithm.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the non-limiting, exemplary embodiments that are illustrated in the accompanying drawings, in which.

DETAILED DESCRIPTION

It is to be understood that the embodiments may assume various alternative variations and step sequences, except where expressly specified to the contrary. It is also to be understood that the specific devices and processes described in the following specification, are simply exemplary embodiments or aspects of the disclosure. Hence, specific dimensions and other physical characteristics related to the embodiments or aspects disclosed herein are not to be considered as limiting. No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Also, as used herein, the terms "has," "have," "having," or the like are intended to be open-ended terms. Further, the phrase "based on" is intended to mean "based at least partially on" unless explicitly stated otherwise.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. A computing device may also be a desktop computer or other form of non-mobile computer. In non-limiting embodiments, a computing device may include an artificial intelligence (AI) accelerator, including an application-specific integrated circuit (ASIC) neural engine such as Apple's M1® "Neural Engine" or Google's TENSOR-FLOW® processing unit. In non-limiting embodiments, a computing device may be comprised of a plurality of individual circuits.

As used herein, the term "subject" may refer to a person (e.g., a human body), an animal, a medical patient, and/or the like. A subject may have a skin or skin-like surface.

In non-limiting embodiments, provided is a system, method, and computer program product for tracking a curved needle in images, such as but not limited to 2D ultrasound images. The system, method, and computer program product in non-limiting embodiments improve upon existing techniques for tracking needles, producing more accurate results and an efficient use of computing resources. Techniques described herein provide a dual-mode tracking approach to track a needle through both visible and low-visibility conditions. The techniques described herein can automatically estimate and utilize kinematic information including needle insertion location, angle, and length. For example, non-limiting embodiments can utilize kinematic information from a needle-inserting robot. Non-limiting embodiments can be used to improve the operability of a needle-inserting robot and improve the accuracy of its operations.

Figure 1:
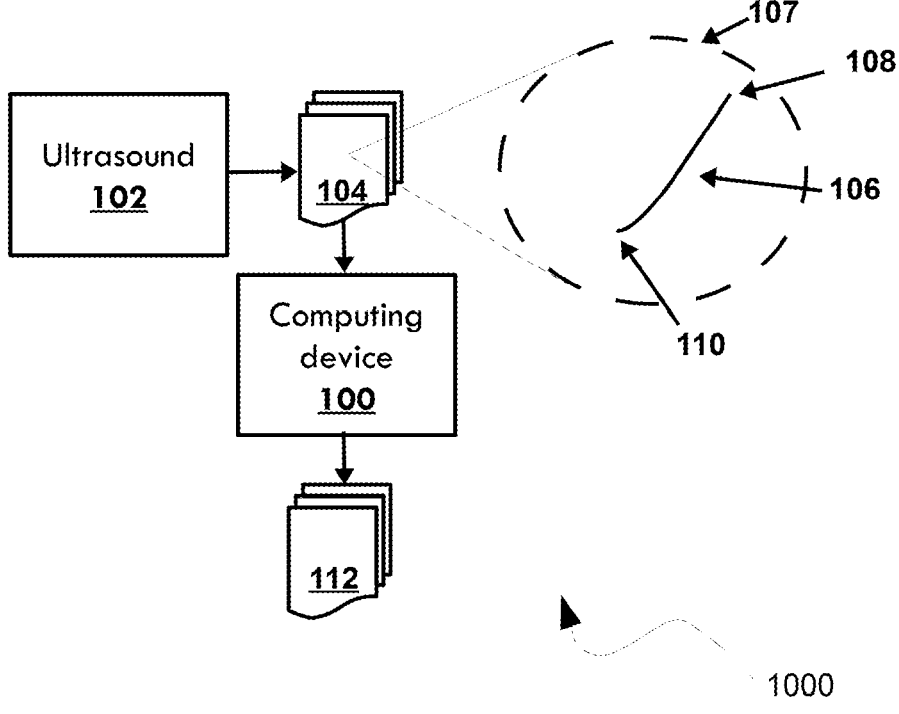
FIG. 1 illustrates a system for tracking a curved needle according to non-limiting embodiments.

FIG. 1 shows a system 1000 for tracking a curved needle 106 being inserted into the tissue in a region 107 of a subject according to non-limiting embodiments. An ultrasound device 102 is used to capture a sequence of images 104 of a subject. It will be appreciated that other imaging techniques and types of image capture devices may be used, and that ultrasound is used herein as an example. The sequence of images 104 represents motion of the needle 106 being inserted into a tissue of a patient. The needle 106 includes an insertion point 108 (e.g., a location relative to the tissue where the needle punctures the skin surface) and a tip 110 (e.g., an end of the needle). In the example shown in FIG. 1, the tip 110 of the needle 106 is bent as it is inserted into the tissue. The sequence of images 104 is processed by a computing device 100 to produce a sequence of segmented images 112 in which the needle is segmented and identified. For example, the sequence of segmented images 112 may include a line or lines overlaid on the raw images to show a predicted needle location. Additionally or alternatively, the sequence of segmented images 112 may include classified pixels identifying the pixels of the needle and/or the pixels of the tip 110 and/or insertion point 108.

Figure 3:
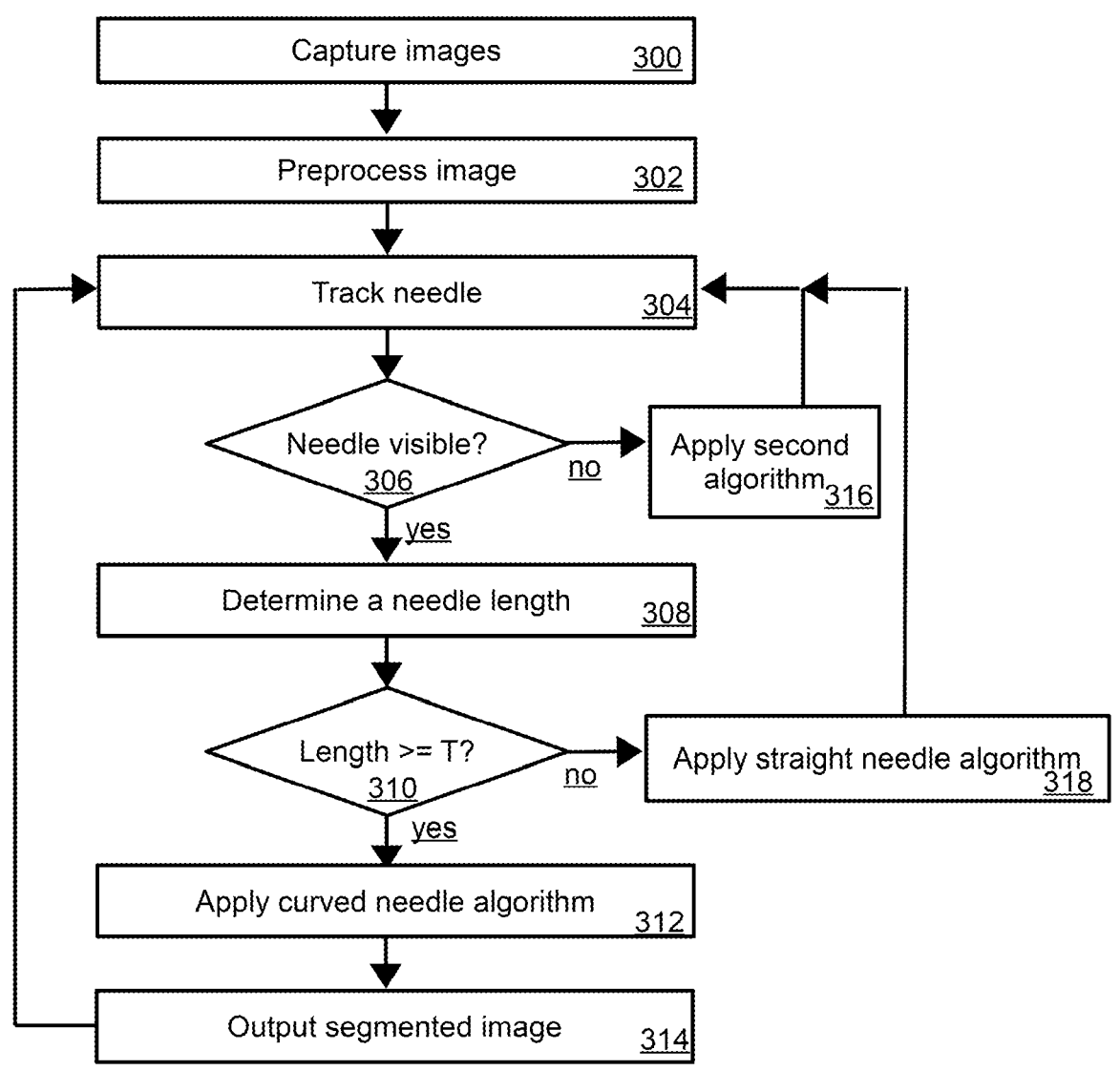
FIG. 3 illustrates a flow diagram for a method of tracking a curved needle according to non-limiting embodiments.

Referring now to FIG. 3, a flow diagram is shown for a method of tracking a curved needle according to non-limiting embodiments. The steps shown in FIG. 3 are for example purposes only. It will be appreciated that additional, fewer, different, and/or a different order of steps may be used in non-limiting embodiments. At a first step 300, a sequence of images is captured with an ultrasound device or other imaging device. In some examples, the sequence of images may have been previously captured and processed from a data storage device. At step 302, one or more images in the sequence of images are pre-processed. For example, each image may be filtered (e.g., with a median filter) to reduce speckle noise. The images may also be cropped to the region that is around the last detected needle. At step 302, during pre-processing, one or more images without the needle may be identified to calculate a background image, which is used to calculate Histogram of Gradient (HoG) thresholds.

With continued reference to FIG. 3, at step 304, tracking of the needle is commenced. The tracking process may be automatically initialized at step 302 by rendering a first line, and automatically calculating the insertion angle, location, and length of the needle. Tracking the needle may start with step 306, in which it is determined if the needle in a given image (e.g., a frame in the sequence of images) satisfies a visibility threshold (e.g., meets and/or exceeds a predetermined threshold value). Additionally or alternatively, step 306 may be performed at any time throughout steps 304, 308, 310, 312, 314, 316, 318. In response to determining that the needle is sufficiently visible, a visible needle segmentation process represented by steps 308, 310, 312, 314, 318 is commenced.

Non-visual knowledge regarding the position of the needle (e.g., where the needle is, where it's coming from, etc.) is obtained from the kinematics information associated with the robot. This kinematics information is used to determine the location of the needle in a low visibility situation (e.g., where the visibility of the needle fails to satisfy a visibility threshold). For example, during use of the robot-controlled needle, the kinematics information can be used to determine how far the needle is inserted. In operation the calibration based on kinematics information of the robot can be inaccurate. Thus, in non-limiting embodiments, in response to determining that the needle is visible (e.g., satisfies a visibility threshold), the kinematics of the robot may be automatically recalibrated using the visible location of the needle. In this manner, the next time that the needle does not satisfy the visibility threshold, the updated, recalibrated kinematics information is used to improve the accuracy of the determination.

In non-limiting embodiments, kinematics data may come from many sources, such as abut not limited to a robot inserting the needle, and/or some device (independent of the ultrasound images) that tracks insertion of the needle by a human. Other data sources are possible.

When the visible needle length is short, straight needle tracking is used, and when the visible needle length is longer, curved needle tracking is used. For example, with continued reference to FIG. 3, at step 308 a needle length is determined. At step 310, it is determined if the needle length satisfies a length threshold (e.g., meets or exceeds a predetermined threshold). If the needle length satisfies a threshold (e.g., is sufficiently long, such as 3 millimeters in an example), the process proceeds to step 312 and a curved needle tracking algorithm is applied to the needle (e.g., a weighted polynomial fitting algorithm). If the needle length does not satisfy the threshold, the process proceeds to step 318 and a straight needle tracking algorithm is applied to the image of the needle. Moreover, if curved needle tracking fails (e.g., results in an error) at step 312, the process may automatically proceed to step 318 in order to revert to straight needle tracking.

The weighted polynomial fitting algorithm applied at step 312 may include selecting a curve with a highest weighted combination of pixels that fit the curve of the needle. The candidate pixels are first selected by intensity thresholding (e.g., determining an intensity of each pixel and determining if it satisfies a threshold). The image may then be filtered (e.g., by a Sobel filter), and the pixel(s) connected to the candidate pixels with large response may also be considered as additional candidate pixels. The weight of each pixel may be calculated as $w_p=w_I \times w_G \times w_T$, where $w_I$ is the normalized intensity in the region of interest (e.g., region 107 in FIG. 1), $w_G$ is the gradient magnitude computed as the normalized response of Sobel filtering, and $w_T$ is the distance of the estimated tip location from the set of pixels. Curved needles are less likely to be fully in-plane, with the pixels near the tip being less bright if partially out-of-plane, so a higher weight may be given to needle-tip pixels when fitting the curve to force it to follow the tip: $w_T=\exp(-(x_T-x)/c)$. The total weight of each curve is $\Sigma_{p \in P} w_p \times w_K$, where P is the set containing all the points close to the curve. A kinematic weight $w_K$ is included to penalize deviation from the insertion location on the side of the image: $w_K=(\log(\max y_{Can} \min y_{Can})+|y_{curve}-y_{insertion}|)$, where $y_{curve}$ is the vertical coordinate of the estimated insertion location of the curve and is calculated by extending the curve to the edge of image, and $y_{Can}$ is the vertical coordinate of all the candidate pixels.

At step 312, the tip of the needle and the insertion point of the needle may be adjusted because the needle may be only partially visible. A line corresponding to the needle is extended to the side of the image and then to the opposite direction until the length of the line is equal to (e.g., within a threshold of) the length of the needle in a previous image. A region (e.g., a range of pixels) surrounding an end of the line may then be searched to identify the tip. For example, a previous consecutive image may be subtracted from the image currently being processed, and one or more pixels with the largest intensity change between the two images may be located and identified as the tip of the needle.

Also at or after step 312, a Kalman filter may be used to smooth and stabilize the tracking of the needle after the needle is segmented for a current image being processed. For different modes, the covariance of the observation R is different. The state and observation of the Kalman filter includes the coordinate of the tip location and insert location, as shown in Equation 3.

$$x = \begin{bmatrix} x^{tip} & y^{tip} & v_x^{tip} & v_y^{tip} & x^{bas} & y^{base} \end{bmatrix} \quad \text{(Equation 3)}$$

$$y = \begin{bmatrix} x^{tip} & y^{tip} & x^{base} & y^{base} \end{bmatrix}$$

The state transition matrix F and observation matrix H are shown Equation $$F = \begin{bmatrix} 1 & 0 & dt & 0 & 0 & 0 \\ 0 & 1 & 0 & dt & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{bmatrix} H = \begin{bmatrix} 1 & 0 & 0 & 0 & 0 & 0 \\ 0 & 1 & 0 & 0 & 0 & 0 \\ 0 & 0 & 0 & 0 & 1 & 0 \\ 0 & 0 & 0 & 0 & 0 & 1 \end{bmatrix} \quad \text{(Equation 4)}$$

The result after the Kalman filter is the final tip and insert point location. If the Kalman filter prediction is similar to the output of the tracking algorithm, the insertion location and insert angle may be updated to a current estimation. In non-limiting embodiments, the Kalman filter may be applied to each processed image, regardless of whether it is a low-visibility process, a visible process, a curved-needle process, or a straight-needle process.

At step 318, the straight needle tracking algorithm may include background subtraction followed by Gabor filtering to enhance the needle image. The angle of the Gabor filter may be based on the needle insertion angle. Thresholding (e.g., using Otsu's thresholding technique) may be used to provide candidate pixels for a probabilistic Hough transformation to locate the straight lines. The final output is the longest line having an angle and insertion location similar to the current estimated insertion angle and location.

At step 306, if it is determined that the needle in an image does not satisfy a visibility threshold, the method may proceed to step 316 to conduct a low-visibility needle segmentation process. Step 316 may be automatically reverted to in response to visible needle tracking failing (e.g., producing an error). The low-visibility segmentation process may implement a HoG feature-based Kernelized Fuzzy C-Mean (KFCM) clustering to estimate tissue deformation and needle location. HoGs are calculated for each cell in the image, and the tissue deformation is detected by comparing the HoG of each cell between a static background image and current image. For example, a cell may be a patch (e.g., a small region) in the image, and a comparison may be made between the patch of a static image and a current image to determine which image region is moving. The background image may be identified during pre-processing at step 302. For each cell I, the HoG of the background image is $$h_b^I$$

and the HoG of each static image s is $$h_s^I,$$

i=1, 2, . . . , k. The threshold vector for each cell $h^1$ is calculated with Equation 1, where i is the index of each element of the threshold vector.

$$h^I(i) = \max_{s=1,2,\dots,N} \left| h_b^I(i) - h_s^I(i) \right| \qquad \text{(Equation 1)}$$

In the new image HoG, [INSERT] is first calculated. The feature of each cell $w^I$ is defined by Equation 2.

$$w_f^I(i) = \begin{cases} 0 & \left| h_b^I(i) - h_f^I(i) \right| <= h^I(i) \\ \left| h_b^I(i) - h_f^I(i) \right| & \text{otherwise} \end{cases} \qquad \text{(Equation 2)}$$

The HoG features are then passed to KFCM clustering. The cells may be clustered into three classes. The class having the largest number of members is determined to be the background. The largest connected regions near (e.g., within a number of pixels) of the insert location is determined to be the region of interest. For example, the largest connected regions no more than one cell away from the cell that the insert location is in may be selected. The main axis of this region is estimated to be the needle location as shown in FIG. 5.

Figure 5:
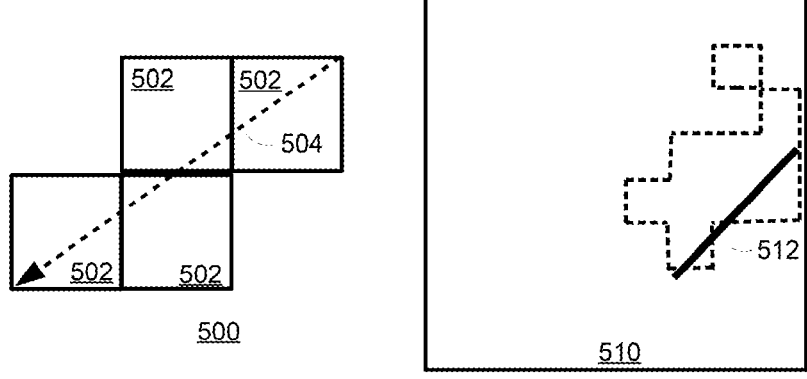
FIG. 5 illustrates a region of interest of an image used in a system and method for tracking a curved needle according to non-limiting embodiments.

Referring now to FIG. 5, shown is an illustration 500 of a main axis 504 of the region of interest, where the region is represented by cells 502. The main axis 504 connects the upper right corner and the lower left corner in the direction of insertion of the needle. Also shown in FIG. 5 is an example output of the segmentation algorithm, where the cells in the image 510 are identified by broken lines, and the needle 512 (following application of a Kalman filter) is shown in bold. These outputs may be colorized, such that the needle 512 is shown in one color (e.g., red) to contrast against the cells (e.g., which may be outlined in blue or green), as an example.

Figure 4:
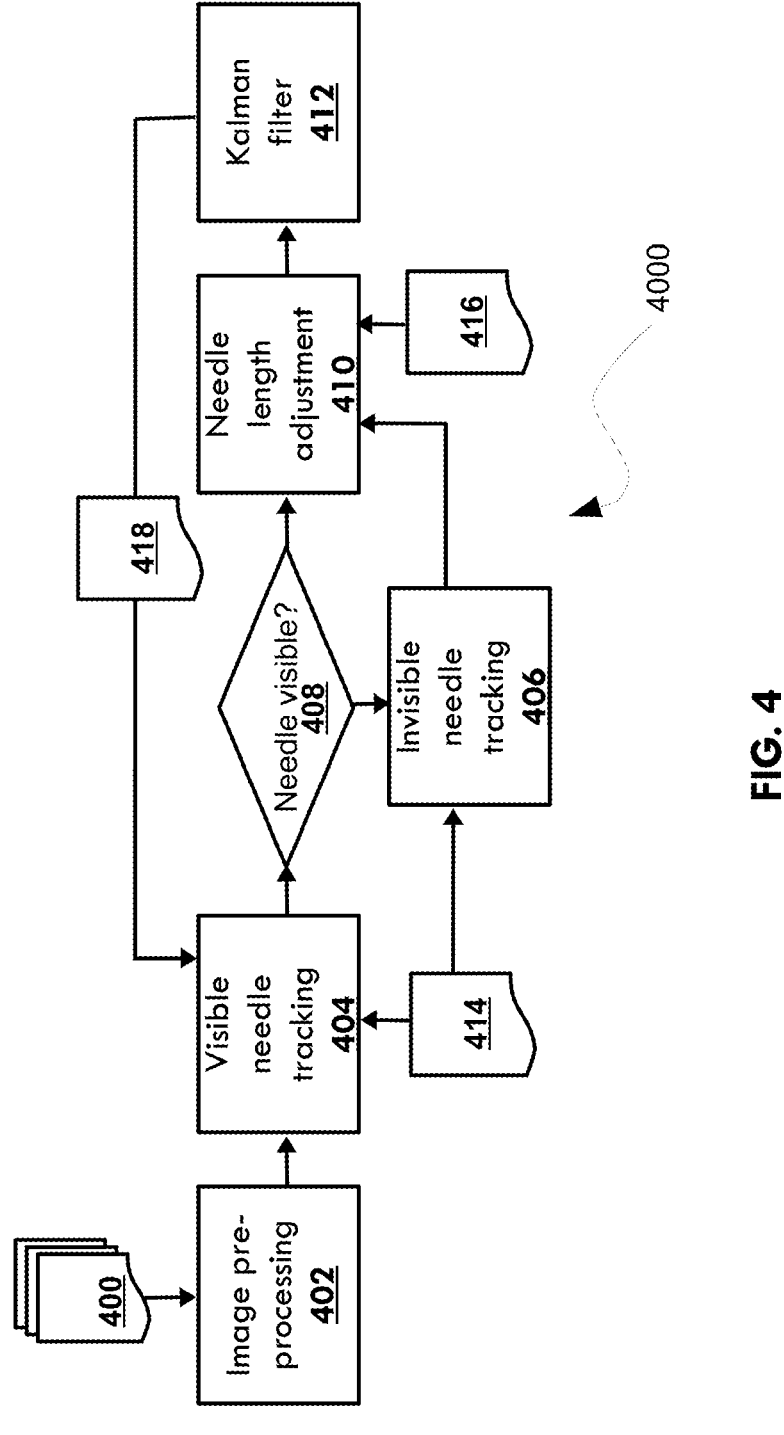
FIG. 4 illustrates a flow diagram for a method of tracking a curved needle according to non-limiting embodiments.

FIG. 4 shows a schematic flow diagram for a method of tracking a curved needle according to non-limiting embodiments. Components 402, 404, 406, 408, 410, 412 represent processing tasks that may be performed by a computing device, by multiple computing devices, by separate software modules and/or hardware modules, by one or more software applications, and/or the like. For example, in non-limiting embodiments, components 402, 404, 406, 408, 410, 412 may be software functions (e.g., modules) performed on one or more computing devices. A sequence of images 400 is input into an image pre-processing module 402, which may pre-process each image as explained herein with respect to step 302 of FIG. 3. The pre-processed images are then input into a visible needle tracking module 404, which also receives, as input, a background image 414, which may also be an output of the image pre-processing module 402. The visible needle tracking module 404 may process each image as explained herein with respect to steps 304, 308, 310, 312, and 318 of FIG. 3. A visibility threshold module 408 may, in some examples, be part of the visible needle tracking module 404 and may repeatedly determine, while tracking the needle, if the needle is sufficiently visible. The visibility threshold module 408 may process the image as explained herein with respect to step 306 in FIG. 3.

With continued reference to FIG. 4, during needle tracking, if the visibility of the needle does not satisfy the visibility threshold, the invisible needle tracking module 406 may be automatically invoked and switched to as a tracking method. The invisible needle tracking module 406 may also receive a background image 414 as input and process each image of the needle as explained herein with respect to step 316 of FIG. 3. The needle length adjustment module 410 receives, as input, a currently processed image and a previous image 416 (e.g., an image that precedes the current image in the sequence of images 400). The needle length adjustment module 410 may process each image as described herein with respect to steps 308, 310, 312 of FIG. 3. A Kalman filter module 412 may receive, as input, an output of the needle length adjustment 410, which includes segmented images that identify the needle, the tip of the needle, and the insertion point of the needle. The Kalman filter module 412 may process the segmented images to smooth and stabilize the tracking of the needle as described herein with respect to step 312 of FIG. 3. The Kalman filter outputs an estimation 418 of needle location, including tip and insertion point location, which is fed back into the visible needle tracking module 404 which uses the previous estimate to determine the next needle displacement.

In non-limiting embodiments, the second algorithm applied at step 316 for a low-visibility image (e.g., where the visibility fails to satisfy a visibility threshold) may utilize detected tissue displacement to track the needle. For example, speckle tracking may be used to determine a displacement of the needle. Speckle is a granular texture that exists in the ultrasound images and produces a texture for displacement tracking. A displacement field may be generated and a global affine motion may be estimated. The global affine motion may be subtracted from the displacement field. Graph-based motion segmentation may be used to divide the tissue displacement into a moving region and a static region. The average direction of the flow in this region and the main axis of the flow region are considered to be candidate needle axis orientations. The algorithm then selects the orientation that is more similar to a template orientation, which is given by an external measurement (such as kinematics) or the orientation of the needle in the last image (e.g., in a prior segmentation).

The optical flow-based speckle tracking technique, Hough transformations, and a kinematics tracking algorithm are used in non-limiting embodiments to determine an estimation of the needle location. The kinematics estimation may be provided by robot kinematics or an external tracking system (such as an optical or magnetic tracking device, e.g. an augmented-reality visor's 3D camera system, ClaroNav's MicronTracker, or NDI's Aurora), which can estimate the tip location relative to the ultrasound probe. The performances of these algorithms may be different in different situations. The algorithm may assign each tracking algorithm with a confidence score from their agreements with the segmentation result in previous images and the similarities between themselves. The confidence scores may be used in the Kalman filter to adjust the observation covariances, making the filter trust the observations with higher confidence scores. In some non-limiting embodiments, automatic compensation may be added in the kinematics tracking to compensate for the error generated in the calibration. The error in the calibration may lead to a stable bias in the estimation of needle location. The algorithm may self-compensate the error based on the pure vision-based segmentation. The algorithm may be configured to estimate the bias when the Hough Transform detects a line similar to the estimation in the prior image.

Non-limiting embodiments of the systems, methods, and computer program products described herein may be performed in real-time (e.g., as images of a subject are captured during a procedure) or at a later time (e.g., using captured and stored images of a subject during the procedure). In non-limiting embodiments, to implement a real-time needle tracking system, multiple processors (e.g., including GPUs) may be used to accelerate the process.

In non-limiting embodiments, an artificial neural network (ANN) may be used to determine a location of a needle or portion thereof in combination with the methods described herein. For example, an ANN may be used to detect a tip of the needle, and the algorithms described herein may be used to detect a shaft and/or insertion point of the needle. Moreover, in non-limiting embodiments, the curved needle tracking process described herein may be used to post-process the output of an ANN (e.g., to address a false positive). Further, although a Kalman filter is described herein as being used to fuse tracking results, in non-limiting embodiments the tracking results from the low-visibility tracking and the visible tracking may be fused with an ANN or other technique. The results may be fused in a manner that also outputs confidence scores for the final segmentation of the images, the needle position estimates, and the needle angle estimates.

Figure 2:
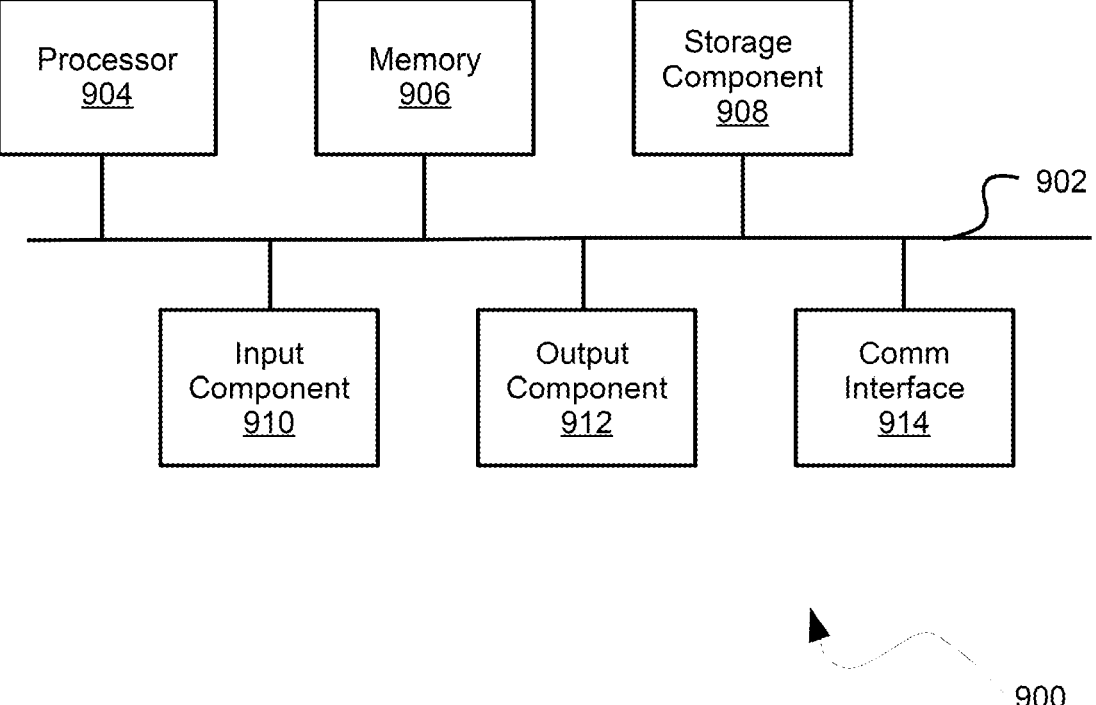
FIG. 2 illustrates example components of a computing device used in connection with non-limiting embodiments

Referring now to FIG. 2, shown is a diagram of example components of a computing device 900 for implementing and performing the systems and methods described herein according to non-limiting embodiments. In some non-limiting embodiments, device 900 may include additional components, fewer components, different components, or differently arranged components than those shown. Device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/ or instructions for use by processor 904.

With continued reference to FIG. 2, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A method for tracking a needle, comprising:

determining a visibility of the needle being inserted into a subject in an image of a sequence of images;

in response to determining that the visibility satisfies a visibility threshold, detecting a location of the needle based on at least one first algorithm and a detected curvature of the needle, wherein detecting the location of the needle based on the at least one first algorithm comprises:

determining a length of a visible portion of the needle while the needle is inserted into the subject; and detecting the location of the needle based on the length of the visible portion of the needle being inserted into the subject;

determining an updated visibility of the needle being inserted into a subject in an image of a sequence of images;

in response to determining that the updated visibility does not satisfy the visibility threshold, detecting an updated location of the needle being inserted based on at least one second algorithm different than the at least one first algorithm; and tracking the location of the needle in the sequence of images based on locations detected with the at least one first algorithm and the at least one second algorithm.

2. The method of claim 1, wherein detecting the location of the needle based on the at least one first algorithm comprises:

determining a length of a visible portion of the needle being inserted into the subject;

in response to determining that the length satisfies a length threshold, detecting the location of the needle based on a weighted polynomial fitting algorithm and the detected curvature of the needle; and in response to determining that the length does not satisfy the length threshold, detecting the location of the needle based on a straight needle tracking algorithm.

3. The method of claim 2, wherein detecting the location of the needle based on the weighted polynomial fitting algorithm comprises:

segmenting the image by identifying candidate pixels corresponding to the needle based on an intensity threshold;

weighing each pixel of the candidate pixels based on a normalized intensity, a gradient magnitude, and a distance to an estimated location of a tip of the needle; and fitting a curve to the candidate pixels based on weights of at least a portion of pixels of the candidate pixels.

4. The method of claim 3, further comprising:

filtering the image after identifying the candidate pixels and before weighing each pixel; and identifying additional candidate pixels based on connections to the candidate pixels.

5. The method of claim 2, wherein detecting the location of the needle based on the straight needle tracking algorithm comprises:

adjusting a location of a tip of the needle and/or an insertion point of the needle.

6. The method of claim 5, wherein adjusting the location of the tip and/or the insertion point comprises:

extending a line corresponding to a visual portion of the needle in a first direction to a side of the image;

extending the line in a second direction opposite the first direction until a length of the line matches a length of the needle in a previous image in the sequence of images; and identifying the tip of the needle in a range of pixels surrounding an end of the line.

7. The method of claim 1, wherein detecting the location of the needle being inserted based on the at least one second algorithm comprises:

calculating a histogram gradient for each cell in the image; and detecting a deformation of tissue based on the histogram gradient of each cell for the image and a static background image.

8. The method of claim 1, wherein detecting the location of the needle being inserted based on the at least one second algorithm comprises:

estimating, with a kinematics tracking algorithm, a location of a tip of the needle based on kinematics data and a compensation factor based on a confidence score.

9. The method claim 1, wherein detecting the location of the needle based on the at least one first algorithm and the detected curvature of the needle comprises:

estimating a main axis of a region of interest including the needle.

10. The method of claim 1, further comprising:

in response to determining that the visibility satisfies a visibility threshold, updating kinematics information associated with the at least one second algorithm.

11. A system for tracking a needle, comprising at least one computing device programmed or configured to:

determine a visibility of the needle being inserted into a subject in an image of a sequence of images;

in response to determining that the visibility satisfies a visibility threshold, detect a location of the needle based on at least one first algorithm and a detected curvature of the needle, wherein detecting the location of the needle based on the at least one first algorithm comprises:

determining a length of a visible portion of the needle while the needle is inserted into the subject; and detecting the location of the needle based on the length of the visible portion of the needle being inserted into the subject;

determining an updated visibility of the needle being inserted into a subject in an image of a sequence of images;

in response to determining that the visibility does not satisfy the visibility threshold, detect the location of the needle being inserted based on at least one second algorithm; and track the location of the needle in the sequence of images based on locations detected with the at least one first algorithm and/or the at least one second algorithm as continuously or continually determined based on comparing the visibility of the needle to the visibility threshold.

12. The system of claim 11, wherein detecting the location of the needle based on the at least one first algorithm comprises:

determining a length of a visible portion of the needle being inserted into the subject;

in response to determining that the length satisfies a length threshold, detecting the location of the needle based on a weighted polynomial fitting algorithm and the detected curvature of the needle; and in response to determining that the length does not satisfy the length threshold, detecting the location of the needle based on a straight needle tracking algorithm.

13. The system of claim 12, wherein detecting the location of the needle based on the weighted polynomial fitting algorithm comprises:

segmenting the image by identifying candidate pixels corresponding to the needle based on an intensity threshold;

weighing each pixel of the candidate pixels based on a normalized intensity, a gradient magnitude, and a distance to an estimated location of a tip of the needle; and fitting a curve to the candidate pixels based on weights of at least a portion of pixels of the candidate pixels.

14. The system of claim 13, the at least one computing device further configured to:

filter the image after identifying the candidate pixels and before weighing each pixel; and identify additional candidate pixels based on connections to the candidate pixels.

15. The system of claim 12, wherein detecting the location of the needle based on the straight needle tracking algorithm comprises:

adjusting a location of a tip of the needle and/or an insertion point of the needle.

16. The system of claim 15, wherein adjusting the location of the tip and/or the insertion point comprises:

extending a line corresponding to a visual portion of the needle in a first direction to a side of the image;

extending the line in a second direction opposite the first direction until a length of the line matches a length of the needle in a previous image in the sequence of images; and identifying the tip of the needle in a range of pixels surrounding an end of the line.

17. The system of claim 11, wherein detecting the location of the needle being inserted based on the at least one second algorithm comprises:

calculating a histogram gradient for each cell in the image; and detecting a deformation of tissue based on the histogram gradient of each cell for the image and a static background image.

18. The system of claim 11, wherein detecting the location of the needle being inserted based on the at least one second algorithm comprises:

estimating, with a kinematics tracking algorithm, a location of a tip of the needle based on kinematics data and a compensation factor based on a confidence score.

19. The system of claim 11, wherein detecting the location of the needle based on the at least one first algorithm and the detected curvature of the needle comprises:

estimating a main axis of a region of interest including the needle.

20. A computer program product for tracking a needle, comprising at least one non-transitory computer-readable medium including instructions that, when executed by at least one computing device, cause the at least one computing device to:

determine a visibility of the needle being inserted into a subject in an image of a sequence of images;

in response to determining that the visibility satisfies a visibility threshold, detect a location of the needle based on at least one first algorithm, a length of a visible portion of the needle, and a detected curvature of the needle;

segment the image identifying candidate pixels corresponding to the needle based on the location of the needle, resulting in a segmented image;

after detecting the location of the needle, determine a new visibility of the needle being inserted into the subject in at least a second image of the sequence of images, resulting in a segmented second image;

in response to determining that the new visibility does not satisfy the visibility threshold, detect a new location of the needle being inserted based on at least one second algorithm;

segment the at least a second image based on the new location; and continue to track the location of the needle in the sequence of images based on the segmented image, the segmented second image, and at least one further segmented image of the sequence of images as continuously or continually determined based on comparing the visibility of the needle to the visibility threshold.

* * * * *